US008883731B2

(12) United States Patent
Takahashi et al.

(10) Patent No.: US 8,883,731 B2
(45) Date of Patent: Nov. 11, 2014

(54) AGENT FOR REDUCING RISK IN ONSET OF DISEASE ASCRIBABLE TO NON-DIPPER CIRCADIAN RHYTHM OF BLOOD PRESSURE

(71) Applicant: CALPIS Co., Ltd., Tokyo (JP)

(72) Inventors: Mari Takahashi, Shibuya-ku (JP); Naoyuki Yamamoto, Sagamihara (JP); Kazuhisa Yamada, Shibuya-ku (JP); Toshirou Iketani, Akiruno (JP)

(73) Assignee: CALPIS Co., Ltd, Tokyo (JP)

( * ) Notice: Subject to any disclaimer, the term of this patent is extended or adjusted under 35 U.S.C. 154(b) by 82 days.

(21) Appl. No.: 13/850,610

(22) Filed: Mar. 26, 2013

(65) Prior Publication Data

US 2013/0210732 A1    Aug. 15, 2013

Related U.S. Application Data

(63) Continuation of application No. 13/292,561, filed on Nov. 9, 2011, now abandoned.

(60) Provisional application No. 61/411,776, filed on Nov. 9, 2010.

(51) Int. Cl.
*A61K 38/06* (2006.01)
*A61K 38/01* (2006.01)

(52) U.S. Cl.
CPC .............. *A61K 38/018* (2013.01); *A61K 38/06* (2013.01)
USPC ....................................... 514/15.6

(58) Field of Classification Search
None
See application file for complete search history.

(56) References Cited

FOREIGN PATENT DOCUMENTS

| EP | 1 669 463 A1 * | 6/2006 | ............ A61P 9/12 |
|---|---|---|---|
| EP | 1669463 A1 * | 6/2006 | |
| JP | 3-120225 A | 5/1991 | |
| JP | 6-040994 A | 2/1994 | |

OTHER PUBLICATIONS

Nakamura, Antihypertensive Effect of Sour Milk and Peptides Isolated from It that are Inhibitors to Angiotensin I-Converting Enzyme, J Dairy Sci, 78:1253-1257, 1995.*
Nakamura et al (J Dairy Sci (1995) 78: 1253-1257).*
Guidelines for the Management of Hypertension, Chapter 2: Blood Pressure Measurement and Clinical Evaluation, The Japanese Society of Hypertension, 2009, pp. 8-17.
"Guidelines for Standard of ABPM," Japanese Circulation Journal, 2000, pp. 1207-1237, vol. 64, Suppl. V.
Germino et al., "The Impact of Lactotripeptides on Blood Pressure Response in Stage 1 and Stage 2 Hypertensives," The Journal of Clinical Hypertension, Mar. 2010, pp. 153-159, vol. 12, No. 3.
Mizuno et al., "Release of Short and Proline-Rich Antihypertensive Peptides from Casein Hydrolysate with an *Aspergillus oryzae* Protease," J. Dairy Sci, 87:3183-3188, 2004.
Sano et al., "Effect of Casein Hydrolysate, Prepared with Protease Derived from *Aspergillus oryzae*, on Subjects with High-Normal Blood Pressure or Mild Hypertension," J Medicinal Food, 8(4): 423-430, 2005.
Nakamura et al., "Antihypertensive Effect of Sour Milk and Peptides Isolated from It that are Inhibitors to Angiotensin I-Converting Enzyme," J Dairy Sci, 78:1253-1257, 1995.
Fernandez et al., "The Human Milk Microbiota: Origin and Potential Roles in Health and Disease," Pharmacological Research, Sep. 10, 2012.
George L. Carrick, "Koumiss, or Fermented Mare's Milk," 1881 (MDCCCLXXXI), William Blackwood and Sons, Edinburgh and London.

* cited by examiner

*Primary Examiner* — Jean Witz
*Assistant Examiner* — Mindy Newman
(74) *Attorney, Agent, or Firm* — Sughrue Mion, PLLC

(57) ABSTRACT

An agent for reducing risk in onset of diseases ascribable to non-dipping circadian profile of blood pressure is provided. This agent is capable of effectively lowering SBP from night to early morning in individuals with non-dipping circadian profile of blood pressure, in particular, normal individuals with normal SBP and DBP among them, and is thus capable of reducing risk in onset, particularly likely in the morning, of diseases caused by circadian variation of blood pressure. The agent is intended for administration to such subjects, and contains a hydrolysate or a concentrate thereof, containing Val-Pro-Pro and Ile-Pro-Pro and obtained by hydrolysis of animal milk protein.

10 Claims, 1 Drawing Sheet

AGENT FOR REDUCING RISK IN ONSET OF DISEASE ASCRIBABLE TO NON-DIPPER CIRCADIAN RHYTHM OF BLOOD PRESSURE

CROSS-REFERENCE TO RELATED APPLICATIONS

This application is a continuation of U.S. patent application Ser. No. 13/292,561, filed Nov. 9, 2011, which is a Non-Provisional U.S. Patent Application of Provisional U.S. Patent Application No. 61/411,776, filed Nov. 9, 2010, the entire disclosures of which are hereby incorporated by reference.

FIELD OF ART

The present invention relates to an agent capable of reducing risk in onset, particularly likely in the morning, of various diseases ascribable to vascular problems, such as cardiovascular or cerebrovascular problems, caused by circadian variation of blood pressure, in individuals with a blunted decline in blood pressure from night to early morning, i.e., so-called "non-dippers", in particular, normotensive individuals with normal 24-hour mean blood pressure among them.

BACKGROUND ART

Hypertension is conventionally known to be a crucial risk factor for many diseases, such as cerebral infarction, myocardial infarction, myocardial ischemia, atherosclerosis, cardiac failure, cerebral stroke, coronary artery diseases, and peripheral vascular diseases.

In light of this, various hypotensive substances have been discovered and used on hypertensive patients. For example, tripeptides, such as Val-Pro-Pro and Ile-Pro-Pro, and casein hydrolysate containing such tripeptides, have been reported to have angiotensin I converting enzyme inhibitory activity (ACEI activity) and exhibit a hypotensive effect (see Patent Publications 1 and 2).

The definition of hypertensive patients is not completely definite, and may vary depending on the environment or apparatus used in measurement. When measured with a recently popularized 24-hour ambulatory blood pressure monitor, individuals with mean systolic blood pressure (SBP)≥130 mmHg and mean diastolic blood pressure (DBP)≥80 mmHg usually fall under the category (see Non-patent Publication 1).

With the spread of the 24-hour ambulatory blood pressure monitors, circadian variation profile of blood pressure has come to be determined by ABPM (ambulatory blood pressure monitoring) and used in categorization and study of risk factors for various diseases (Non-patent Publication 2).

Circadian profile of blood pressure in humans generally tends to be high in daytime and decline through nighttime to early morning. With regard to such blood pressure profile, it is known to categorize individuals with a ≥10% decline in nighttime mean SBP compared with daytime measurements as dippers, and those with a <10% decline as non-dippers (Non-patent Publication 3), but there is currently no definite provision of classification criteria for dippers and non-dippers. At any rate, it has been reported that individuals with non-dipping circadian profile of blood pressure are more likely to develop cerebral infarction, myocardial infarction, myocardial ischemia, atherosclerosis, cardiac failure, cerebral stroke, coronary artery diseases, peripheral vascular disease, and the like in the morning than dippers.

It has also been revealed that such a trend is observed not only in hypertensive patients, but also in healthy individuals with normal 24-hour mean blood pressure.

Various kinds of hypotensive drugs for hypertensive patients are generally known, including those reducing daytime blood pressure, and those reducing the entire circadian blood pressure with long-lasting efficacy. However, little is known about drugs for approximating mean SBP from night to early morning in normotensive non-dippers, who are conventionally considered not to require hypotensive drugs, to the profile of dippers.

Patent Publications
Patent Publication 1: JP-6-40994-A
Patent Publication 2: JP-3-120225-A
Non-Patent Publications
Non-Patent Publication 1: *Guidelines for the Management of Hypertension* 2009, Chapter 2: *Ketsuatsu Sokutei to Rinsho Hyoka* (Blood Pressure Measurement and Clinical Evaluation), p 8-17 (2009), The Japanese Society of Hypertension
Non-Patent Publication 2: Japanese Circulation Journal Vol. 64, Suppl. V, (2000), "24-*jikan Ketsuatsukei no Shiyou* (*ABPM*) *Kijun ni Kansuru Gaidorain* (Guidelines for Standard of ABPM)", p 1207-1237
Non-Patent Publication 3: "The Impact of Lactotripeptides on Blood Pressure Response in Stage 1 and Stage 2 Hypertensives", The Journal of Clinical Hypertension, Vol. 12, No. 3, p 153-159 (2010)

SUMMARY OF THE INVENTION

It is an object of the present invention to provide an agent capable of reducing risk in onset, particularly likely in the morning, of diseases ascribable to circadian variation of blood pressure in individuals with a blunted decline in blood pressure from night to early morning, i.e., so-called "non-dippers", in particular, normotensive non-dippers with normal 24-hour mean blood pressure.

According to the present invention, there is provided an agent for reducing risk in onset of a disease ascribable to non-dipping circadian profile of blood pressure, said agent comprising a hydrolysate or a concentrate thereof, containing Ile-Pro-Pro and Val-Pro-Pro and obtained by hydrolysis of animal milk protein, wherein said agent is for oral intake by a non-dipper individual with a less than 10% decline in mean systolic blood pressure during a period 0:00-5:00 compared to mean systolic blood pressure during a period 8:00-21:00, brachially measured every 30 minutes with a 24-hour ambulatory blood pressure monitor, in particular by an individual with mean systolic blood pressure (SBP) of less than 130 mmHg and mean diastolic blood pressure (DBP) of less than 80 mmHg, as measured brachially every 30 minutes with a 24-hour ambulatory blood pressure monitor (sometimes referred to as the present reducing agent hereinbelow).

The present reducing agent is capable of effectively reducing systolic blood pressure from night to early morning in individuals with non-dipping circadian profile of blood pressure, in particular, normal individuals with normal SBP and DBP among them, and can be expected to reduce the risk in onset, particularly likely in the morning, of various diseases ascribable to circadian variation of blood pressure, such as cerebral infarction, myocardial infarction, myocardialischemia, atherosclerosis, cardiac failure, cerebral stroke, coronary artery diseases, and peripheral vascular diseases.

PREFERRED EMBODIMENTS OF THE INVENTION

Figure 1:
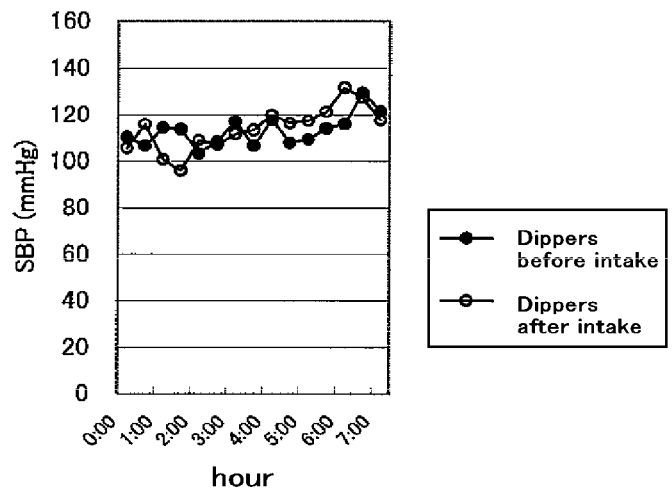
FIG. 1 is a graph comparing SBP profiles in dippers before and after the intake of the agent of the present invention for determination of the effect of reducing risk in onset of diseases ascribable to circadian variation of blood pressure, performed in Example 1.

The present invention will now be explained in detail.

The present reducing agent is intended for non-dippers with a <10% decline in mean SBP during the period 0:00-5:00 compared to mean SBP during the period 8:00-21:00, brachially measured every 30 minutes with a 24-hour ambulatory blood pressure monitor, in particular, among them, for individuals with mean SBP<130 mmHg and mean DBP<80 mmHg as measured brachially every 30 minutes with a 24-hour ambulatory blood pressure monitor. The latter individuals are usually not designated as hypertensive patients even if they are non-dippers, and do not need to take hypotensive drugs. However, it has recently been revealed that non-dippers with a blunted nocturnal or early morning decline in blood pressure have higher risk in onset of diseases ascribable to circadian variation of blood pressure, compared to dippers. The present invention enables reduction of this risk by increasing the magnitude of nocturnal or early morning decline in blood pressure in individuals with such high risk.

The present reducing agent contains a hydrolysate or a concentrate thereof, containing VPP and IPP and obtained by hydrolysis of animal milk protein.

The animal milk protein may be from, for example, cow's milk, horse's milk, sheep's milk, goat's milk, or processed milk thereof, such as skim milk, reconstituted milk, powdered milk, or condensed milk, with cow's milk or processed milk thereof being particularly preferred. Protein contained in such milk is known to include sequences VPP and IPP.

The solid content of the animal milk is not particularly limited, and when skim milk is used, the solid non-fat content may usually be about 3 to 15 mass %, preferably 6 to 15 mass % in view of productivity.

The hydrolysate for the present reducing agent is obtained by hydrolyzing animal milk protein so as to obtain IPP and VPP, preferably not less than 3 μg/ml, more preferably 30 μg/ml to 60 μg/ml, most preferably 30 μg/ml to 40 μg/ml of VPP, and not less than 2 μg/ml, more preferably 20 μg/ml to 40 μg/ml, most preferably 20 μg/ml to 30 μg/ml of IPP.

The hydrolysis may be carried out, for example, by (A) fermenting a starting material containing animal milk protein with lactic acid bacteria to obtain a fermentation product, (B) enzymatically digesting a starting material containing animal milk protein with enzymes, or combinations of (A) and (B).

In method (A), the lactic acid bacteria may be, for example, those of the genus *Streptococcus, Lactococcus, Lactobacillus*, or *Bifidobacterium*, with *Lactobacillus* being preferred. Specifically, the lactic acid bacteria of the genus *Lactobacillus* may be, for example, *Lactobacillus bulgaricus, Lactobacillus helveticus, Lactobacillus casei, Lactobacillus acidophilus*, or *Lactobacillus fermentum*, with *Lactobacillus helveticus* being preferred for its excellent efficiency of IPP and VPP production.

Still more specifically, the lactic acid bacteria of the species *Lactobacillus helveticus* may be, for example, *Lactobacillus helveticus* ATCC 15009, *Lactobacillus helveticus* ATCC 521, or *Lactobacillus helveticus* CM4 strain (referred to as CM4 hereinbelow). CM4 has been deposited under the accession number FERM BP-6060 at International Patent Organism Depositary, National Institute of Advanced Industrial Science and Technology, Japan, under the Budapest Treaty on the International Recognition of the Deposit of Microorganisms for the Purposes of Patent Procedure, and has already been patented.

The lactic acid bacteria are preferably in the form of a precultured starter having sufficient activity. The initial cell count of the starter is preferably about $10^5$ to $10^9$ cells/ml.

In order to improve taste and flavor as well as palatability of the resulting fermentation product, yeast may additionally be used in the fermentation. The strains of the yeast are not particularly limited, and for example, yeast of the genus *Saccharomyces*, such as *Saccharomyces cerevisiae*, may preferably be used. The content of the yeast may suitably be selected depending on the desired result.

The fermentation may be carried out by culturing one or more kinds of the above-mentioned lactic acid bacteria in a media, or by mixing and culturing one or more kinds of the above-mentioned lactic acid bacteria and one or more kinds of the above-mentioned yeast together in a media.

The media may be a starting material media containing the animal milk protein, to which secondary components may optionally be added, including yeast extract, vitamins such as ascorbic acid, amino acid such as cysteine, salts such as sodium chloride, sugars such as glucose, sucrose, raffinose, or stachyose, stabilizers such as gelatin, or flavoring agents.

The fermentation may be carried out so as to produce VPP and IPP, for example, usually by static or stirred culture at 25 to 50° C., preferably 30 to 45° C., for 6 to 30 hours, preferably 10 to 24 hours. The fermentation may be started at pH 6.0 to 7.0 and terminated at the cell count$\geq 10^7$ cells/ml and pH$\geq 5.0$. The animal milk protein may be subjected to high temperature pasteurization or the like, before fermentation.

In method (B), the enzymes may preferably be, for example, those containing peptidases which can cleave the Pro-Xaa sequence at the carboxy terminal of Xaa-Pro-Xaa or Xaa-Pro-Pro-Xaa in animal milk protein.

The enzymes may preferably contain serine proteases having serine at their active center, or metalloproteinases having a metal at their active center. The metalloproteinases may be neutral protease I, neutral protease II, leucine amino peptidase, or the like. With at least one of these metalloproteinases, the objective hydrolysate may be obtained efficiently in a short time, and even in a one-step reaction, thus being preferred. The peptidases capable of cleaving the Pro-Xaa sequence may preferably be enzymes having isoelectric points in the acid region.

The enzymes may be, for example, a group of enzymes derived from koji mold, such as *Aspergillus oryzae*. Such a group of enzymes may be obtained by culturing the bacterial cells in a suitable media and extracting the produced enzymes with water, and may preferably be a group of enzymes derived from *Aspergillus oryzae* and having isoelectric points in the acid region.

The group of enzymes derived from *Aspergillus oryzae* may be a commercial product, such as SUMIZYME FP, LP, or MP (registered trademarks, manufactured by SHIN NIHON CHEMICAL CO., LTD.), UMAMIZYME (registered trademark, manufactured by AMANO ENZYME INC.), STERNZYME B11024, PROHIDROXYAMPL (both trade names, manufactured by HIGUCHI, INC.), ORIENTASE ONS (registered trademark, manufactured by HANKYU BIOINDUSTRY CO.), or DENAZYME AP (registered trademark, manufactured by NAGASE BIOCHEMICALS, LTD.), with SUMIZYME FP (registered trademark, manufactured by SHIN NIHON CHEMICAL CO., LTD.) being particularly preferred.

Such a commercially available group of enzymes usually have prescribed optimum conditions, but conditions, such as the amount of enzymes used and the reaction time, may suitably be adjusted depending on the group of enzymes used so as to obtain the objective hydrolysate.

The amount of the enzymes to be added may be such that the ratio of the enzymes to the animal milk protein by mass is, for example, not less than 1/1000, preferably 1/1000 to 1/10, more preferably 1/100 to 1/10, still more preferably 1/40 to 1/10 in an aqueous solution of the animal milk protein.

The reaction conditions may suitably be selected depending on the enzymes so as to obtain the objective hydrolysate. The temperature may usually be 25 to 60° C., preferably 45 to 55° C., the pH may usually be 3 to 10, preferably 5 to 9, more preferably 5 to 8, and the duration of the enzymatic reaction may usually be 2 to 48 hours, preferably 7 to 15 hours.

The enzymatic reaction may be terminated by inactivating the enzymes, usually at 60 to 110° C.

The hydrolysate obtained by method (A), (B), or combinations thereof, may be cleared of precipitate therein, as required, by centrifugation or various filtering.

Further, the obtained hydrolysate may also be cleared of, as necessary, peptides having bitter taste or odor. Such bitter or odorous components may be removed using activated carbon or hydrophobic resins. For example, activated carbon may be added to the obtained hydrolysate at 1 to 20 mass % of the animal milk protein used, and reacted for 1 to 10 hours. The used activated carbon may be removed by a conventional process, such as centrifugation or membrane process operation.

The obtained hydrolysate may be used as a present reducing agent as it is, or after concentrated and dried into powders for improved versatility.

Such powders may optionally contain various auxiliary additives for improving nutritional balance or taste and flavors, such as various carbohydrates, lipids, vitamins, minerals, sweeteners, flavoring agents, pigments, or texture improvers.

The dose of the present reducing agent for a human subject is usually 1 mg to 30 g, preferably about 20 mg to 20 g of the hydrolysate in terms of solids per day, and may be administered in a plurality of doses per day.

The dosing period is usually not less than one day, preferably not less than 20 days, preferably continuously or intermittently. The administration is made orally.

The dosage form of the present reducing agent may be, for example, tablets, pills, hard capsules, soft capsules, microcapsules, powders, granules, or liquid.

The present reducing agent may be formulated, for example, with pharmaceutically acceptable carriers, adjuvants, excipients, auxiliary excipients, antiseptics, stabilizers, binders, pH regulators, buffers, thickeners, gelatinizers, preservatives, and/or antioxidants, as required, and manufactured in unit dose form required for generally accepted formulation.

In formulating the present reducing agent, in expectation of improving the effects of the present invention, conventional hypotensive agents may also be used in combination with the present reducing agent. Further, the effects of the present invention are expected to be enhanced by combination with other drugs having known normalizing effect on the non-dipping profile, such as olmesartan or arotinolol.

The present reducing agent may optionally contain components used in food and beverages, such as sugars, proteins, lipids, stabilizers, vitamins, minerals, flavoring agents, or mixtures thereof, as necessary in addition to the hydrolysate.

EXAMPLES

The present invention will now be explained in detail with reference to Examples, which are illustrative only and not intended to limit the present invention.

Example 1

Preparation of CM4-Fermented Milk

Commercially available skim milk was dissolved in distilled water at a solid content (w/w) of 9%, subjected to high temperature pasteurization in an autoclave at 105° C. for 10 minutes, and cooled to room temperature. The solution was inoculated with 3% (v/w) CM4 starter fermentation liquid (cell count $5 \times 10^8$ cells/ml), and fermented under standing conditions at 37° C. for 24 hours to thereby obtain a CM4-fermented milk.

<Determination of IPP and VPP Contents in CM4-Fermented Milk>

One milliliter of CM4-fermented milk was centrifuged as it is at 15000 rpm for 10 minutes, and the supernatant (whey) was collected. Then 0.3 ml of the whey was poured onto a Sep-Pak cartridge (manufactured by NIHON WATERS K.K.) for adsorption thereon. The cartridge was then washed with distilled water, and subjected to elution with 5 ml of methanol. The eluate was vacuum-dried under centrifugation, and the obtained dried product was dissolved in 0.3 ml of a 0.05% aqueous solution of trifluoroacetic acid. The resulting solution was subjected to HPLC analysis under the following conditions: Apparatus Models Used: HITACHI L4000 UV detector (detected at 215 nm), L6200 intelligent pump, L5030 column oven (35° C.); Separation Condition: flow rate 0.5 ml/min, eluting solvent: 0.3 M NaCl, aqueous solution column of 0.05% trifluoroacetic acid: tradename Asahipak GS320 ($\Phi 3.9 \times 600$ mm).

As a result, it was determined that the contents of VPP and IPP in the CM4-fermented milk whey were 38.5 μg/ml and 23.5 μg/ml, respectively.

<Preparation of Fermented Milk Product for Subjects>

To the CM4-fermented milk prepared above, a stabilizer, sweeteners, flavoring agents, and water were added, which was then homogenized, packed in glass bottles by 160 ml, and pasteurized at 85° C., to thereby obtain a fermented milk product for subjects. The results of the componential analysis of the fermented milk product for subjects are shown in Table 1. The contents of VPP and IPP in the fermented milk product for subjects in the daily dose were 2.53 mg and 1.52 mg, respectively.

TABLE 1

| Component | Content (per 100 g) |
| --- | --- |
| Protein (g) | 1.3 |
| Sugar (g) | 3.4 |
| Ash (g) | 0.4 |
| Lipid (g) | 0 |
| Dietary fiber (g) | 0.7 |
| Water (g) | 94.2 |
| Maltitol (g) | 1.1 |
| Calorie (kJ) | 71 |
| Potassium (mg) | 68 |
| Calcium (mg) | 49 |
| Phosphorus (mg) | 39 |

TABLE 1-continued

| Component | Content (per 100 g) |
|---|---|
| Sodium (mg) | 70 |
| Val-Pro-Pro (VPP) (mg) | 1.58 |
| Ile-Pro-pro (IPP) (mg) | 0.95 |

In the Table, maltitol is included in sugar; potassium, calcium, phosphorus and sodium in ash; and VPP and IPP in protein.

<Selection of Normotensive Dipper and Non-Dipper Subjects>

Twelve subjects aged 55 to 71 who are untreated with antihypertensive medications and have not been suffered from severe hypertension, allergic asthma, severe hepatic or renal diseases, cerebral stroke, or myocardial infarction, were subjected to the following blood pressure determination.

Each subject wore a 24-hour ambulatory blood pressure monitor (model ES-H531 manufactured by TERUMO CORPORATION) on the non-dominant upper arm, and SBP, DBP, and heart rate were measured every 30 minutes over 24 hours.

As a result of the measurements, six subjects were selected who had 24-hour mean SBP<130 mmHg, 24-hour mean DBP≤80 mmHg, and no abnormality in heart rate.

From the results of the blood pressure determination of the six selected subjects, percentage decline of mean SBP during the period 0:00-5:00 from mean SBP during the period 8:00-21:00 was calculated, and the subjects with percentage decline ≥10% were categorized as dippers and the subjects with percentage decline <10% as non-dippers.

As a result, three of the subjects (Subjects 4, 6, and 10) were normotensive dippers, and the other three of the subjects (Subjects 3, 8, and 9) were normotensive non-dippers. Of the data of each selected subject, SBP data and DBP data of the dippers are shown in Tables 2 and 3, respectively, and the SBP data and the DBP data of the non-dippers are shown in Tables 4 and 5, respectively. Incidentally, no fluctuation was observed in the heart rate of the subjects during the determination.

TABLE 2

| | Subject #4 | Subject #6 | Subject #10 |
|---|---|---|---|
| SBP before Dipper | | | |
| 8:00 | 123 | 125 | 133 |
| 8:30 | 117 | 131 | 124 |
| 9:00 | 135 | 116 | 148 |
| 9:30 | 129 | 112 | 152 |
| 10:00 | 124 | 116 | 123 |
| 10:30 | 131 | 134 | 141 |
| 11:00 | 131 | 143 | 130 |
| 11:30 | 129 | 127 | 117 |
| 12:00 | 111 | 140 | 112 |
| 12:30 | 121 | 136 | 106 |
| 13:00 | 121 | 145 | 104 |
| 13:30 | 130 | 135 | 112 |
| 14:00 | 120 | 139 | 118 |
| 14:30 | 114 | 126 | 106 |
| 15:00 | 123 | 139 | 131 |
| 15:30 | 124 | 102 | 124 |
| 16:00 | 166 | 111 | 105 |
| 16:30 | 133 | 120 | 118 |
| 17:00 | 131 | 127 | 120 |
| 17:30 | 138 | 120 | 119 |
| 18:00 | 118 | 129 | 125 |
| 18:30 | 129 | 123 | 118 |
| 19:00 | 124 | 113 | 146 |

TABLE 2-continued

| | Subject #4 | Subject #6 | Subject #10 |
|---|---|---|---|
| 19:30 | 140 | 131 | 116 |
| 20:00 | 130 | 136 | 115 |
| 20:30 | 122 | 138 | 123 |
| 21:00 | 128 | 147 | 122 |
| 21:30 | 101 | 154 | 109 |
| 22:00 | 93 | 161 | 119 |
| 22:30 | 123 | 139 | 125 |
| 23:00 | 105 | 131 | 118 |
| 23:30 | 100 | 116 | 119 |
| 0:00 | 106 | 106 | 119 |
| 0:30 | 109 | 109 | 102 |
| 1:00 | 118 | 114 | 111 |
| 1:30 | 118 | 107 | 116 |
| 2:00 | 106 | 107 | 97 |
| 2:30 | 107 | 113 | 106 |
| 3:00 | 115 | 118 | 118 |
| 3:30 | 93 | 132 | 95 |
| 4:00 | 123 | 112 | 118 |
| 4:30 | 120 | 102 | 102 |
| 5:00 | 97 | 120 | 111 |
| 5:30 | 116 | 104 | 122 |
| 6:00 | 117 | 115 | 116 |
| 6:30 | 123 | 121 | 145 |
| 7:00 | 105 | 101 | 159 |
| 7:30 | 121 | 106 | 118 |
| SBP before | | | |
| 24 hr mean BP | 120.0 | 123.9 | 119.9 |
| 8:00-21:00 (mean daytime) | 127.5 | 128.2 | 122.5 |
| 0:00-5:00 (mean nighttime) | 110.2 | 112.7 | 108.6 |

TABLE 3

| | Subject #4 | Subject #6 | Subject #10 |
|---|---|---|---|
| DBP before Dipper | | | |
| 8:00 | 88 | 75 | 72 |
| 8:30 | 85 | 67 | 70 |
| 9:00 | 81 | 70 | 83 |
| 9:30 | 82 | 65 | 94 |
| 10:00 | 91 | 70 | 81 |
| 10:30 | 88 | 92 | 76 |
| 11:00 | 89 | 79 | 67 |
| 11:30 | 76 | 71 | 70 |
| 12:00 | 74 | 71 | 69 |
| 12:30 | 77 | 78 | 70 |
| 13:00 | 77 | 90 | 73 |
| 13:30 | 81 | 77 | 80 |
| 14:00 | 78 | 87 | 69 |
| 14:30 | 74 | 69 | 70 |
| 15:00 | 78 | 68 | 96 |
| 15:30 | 76 | 64 | 76 |
| 16:00 | 95 | 60 | 61 |
| 16:30 | 82 | 74 | 67 |
| 17:00 | 78 | 72 | 75 |
| 17:30 | 82 | 69 | 75 |
| 18:00 | 79 | 78 | 74 |
| 18:30 | 87 | 73 | 77 |
| 19:00 | 87 | 64 | 71 |
| 19:30 | 85 | 67 | 61 |
| 20:00 | 82 | 70 | 80 |
| 20:30 | 84 | 73 | 73 |
| 21:00 | 87 | 72 | 72 |
| 21:30 | 58 | 73 | 67 |
| 22:00 | 61 | 85 | 67 |
| 22:30 | 80 | 75 | 74 |
| 23:00 | 60 | 74 | 70 |
| 23:30 | 61 | 64 | 73 |
| 0:00 | 66 | 74 | 69 |
| 0:30 | 67 | 74 | 55 |
| 1:00 | 68 | 72 | 63 |

TABLE 3-continued

|  | Subject #4 | Subject #6 | Subject #10 |
|---|---|---|---|
| 1:30 | 66 | 66 | 65 |
| 2:00 | 74 | 66 | 57 |
| 2:30 | 74 | 65 | 60 |
| 3:00 | 68 | 74 | 65 |
| 3:30 | 59 | 71 | 62 |
| 4:00 | 83 | 68 | 64 |
| 4:30 | 77 | 64 | 59 |
| 5:00 | 63 | 68 | 65 |
| 5:30 | 71 | 69 | 68 |
| 6:00 | 80 | 67 | 58 |
| 6:30 | 80 | 71 | 80 |
| 7:00 | 67 | 59 | 81 |
| 7:30 | 74 | 63 | 88 |
| DBP before |  |  |  |
| 24 hr mean BP | 76.7 | 71.4 | 71.1 |
| 8:00-21:00 (mean daytime) | 82.3 | 72.8 | 74.1 |
| 0:00-5:00 (mean nighttime) | 69.5 | 69.3 | 62.2 |

TABLE 4

|  | Subject #3 | Subject #8 | Subject #9 |
|---|---|---|---|
| SBP before Nondipper |  |  |  |
| 8:00 | 109 | 130 | 139 |
| 8:30 | 109 | 135 | 137 |
| 9:00 | 127 | 143 | 141 |
| 9:30 | 115 | 158 | 119 |
| 10:00 | 126 | 134 | 126 |
| 10:30 | 109 | 134 | 111 |
| 11:00 | 118 | 127 | 126 |
| 11:30 | 135 | 121 | 122 |
| 12:00 | 119 | 118 | 130 |
| 12:30 | 118 | 111 | 128 |
| 13:00 | 111 | 120 | 138 |
| 13:30 | 120 | 100 | 118 |
| 14:00 | 110 | 104 | 125 |
| 14:30 | 102 | 101 | 121 |
| 15:00 | 102 | 95 | 121 |
| 15:30 | 115 | 96 | 115 |
| 16:00 | 82 | 99 | 108 |
| 16:30 | 111 | 138 | 126 |
| 17:00 | 129 | 133 | 105 |
| 17:30 | 140 | 135 | 124 |
| 18:00 | 138 | 128 | 134 |
| 18:30 | 142 | 137 | 136 |
| 19:00 | 137 | 139 | 138 |
| 19:30 | 130 | 132 | 141 |
| 20:00 | 112 | 115 | 125 |
| 20:30 | 126 | 116 | 116 |
| 21:00 | 131 | 124 | 119 |
| 21:30 | 131 | 117 | 109 |
| 22:00 | 120 | 129 | 114 |
| 22:30 | 109 | 96 | 73 |
| 23:00 | 119 | 100 | 101 |
| 23:30 | 122 | 95 | 103 |
| 0:00 | 128 | 96 | 103 |
| 0:30 | 116 | 102 | 97 |
| 1:00 | 102 | 120 | 116 |
| 1:30 | 109 | 126 | 112 |
| 2:00 | 101 | 111 | 122 |
| 2:30 | 89 | 115 | 122 |
| 3:00 | 99 | 128 | 115 |
| 3:30 | 110 | 114 | 131 |
| 4:00 | 116 | 124 | 116 |
| 4:30 | 109 | 125 | 115 |
| 5:00 | 111 | 139 | 121 |
| 5:30 | 118 | 125 | 128 |
| 6:00 | 117 | 137 | 126 |
| 6:30 | 128 | 141 | 137 |

TABLE 4-continued

|  | Subject #3 | Subject #8 | Subject #9 |
|---|---|---|---|
| 7:00 | 121 | 143 | 140 |
| 7:30 | 129 | 141 | 156 |
| SBP before |  |  |  |
| 24 hr mean BP | 117.2 | 121.8 | 121.8 |
| 8:00-21:00 (mean daytime) | 119.4 | 123.1 | 125.5 |
| 0:00-5:00 (mean nighttime) | 108.2 | 118.2 | 115.5 |

TABLE 5

|  | Subject #3 | Subject #8 | Subject #9 |
|---|---|---|---|
| DBP before Nondipper |  |  |  |
| 8:00 | 73 | 85 | 83 |
| 8:30 | 69 | 98 | 81 |
| 9:00 | 66 | 89 | 84 |
| 9:30 | 58 | 89 | 82 |
| 10:00 | 72 | 97 | 75 |
| 10:30 | 70 | 65 | 73 |
| 11:00 | 64 | 84 | 78 |
| 11:30 | 78 | 84 | 79 |
| 12:00 | 74 | 89 | 74 |
| 12:30 | 50 | 75 | 88 |
| 13:00 | 59 | 76 | 77 |
| 13:30 | 67 | 65 | 74 |
| 14:00 | 60 | 64 | 84 |
| 14:30 | 55 | 63 | 81 |
| 15:00 | 58 | 60 | 75 |
| 15:30 | 60 | 62 | 74 |
| 16:00 | 38 | 68 | 73 |
| 16:30 | 67 | 50 | 76 |
| 17:00 | 60 | 79 | 71 |
| 17:30 | 81 | 76 | 71 |
| 18:00 | 94 | 87 | 80 |
| 18:30 | 108 | 98 | 76 |
| 19:00 | 111 | 83 | 82 |
| 19:30 | 82 | 92 | 81 |
| 20:00 | 73 | 81 | 98 |
| 20:30 | 73 | 82 | 79 |
| 21:00 | 71 | 76 | 75 |
| 21:30 | 69 | 82 | 78 |
| 22:00 | 60 | 72 | 74 |
| 22:30 | 56 | 64 | 45 |
| 23:00 | 66 | 63 | 48 |
| 23:30 | 62 | 62 | 62 |
| 0:00 | 57 | 63 | 62 |
| 0:30 | 61 | 65 | 54 |
| 1:00 | 63 | 74 | 66 |
| 1:30 | 64 | 74 | 77 |
| 2:00 | 56 | 78 | 73 |
| 2:30 | 54 | 76 | 72 |
| 3:00 | 54 | 79 | 58 |
| 3:30 | 56 | 79 | 72 |
| 4:00 | 58 | 84 | 76 |
| 4:30 | 57 | 77 | 60 |
| 5:00 | 57 | 86 | 65 |
| 5:30 | 64 | 82 | 72 |
| 6:00 | 65 | 83 | 76 |
| 6:30 | 68 | 84 | 79 |
| 7:00 | 68 | 82 | 85 |
| 7:30 | 59 | 75 | 77 |
| DBP before |  |  |  |
| 24 hr mean BP | 65.9 | 77.1 | 74.1 |
| 8:00-21:00 (mean daytime) | 70.0 | 78.4 | 78.7 |
| 0:00-5:00 (mean nighttime) | 57.9 | 75.9 | 66.8 |

<Determination of Capability of Reducing Risk in Onset of Diseases Caused by Circadian Variation of Blood Pressure>

The normotensive dippers and non-dippers selected above were freed of antihypertensive medications for 4 weeks without changing their lifestyle, and then given 160 ml of the fermented milk product for subjects every morning after getting out of bed for 1 month.

On the next day after the final intake, each subject wore a 24-hour ambulatory blood pressure monitor (model ES-H531 manufactured by TERUMO CORPORATION) on the non-dominant upper arm, and SBP, DBP, and heart rate were measured every 30 minutes from 8:00 in the morning over 24 hours under free activity.

The time period 0:00-7:00 was assumed to be the time zone from night to the morning of circadian variation of blood pressure at risk of onset of diseases, and SBP values before and after the intake of the fermented milk product for subjects were compared. The results of the dippers are shown in FIG. 1, and the non-dippers in FIG. 2.

Figure 2:
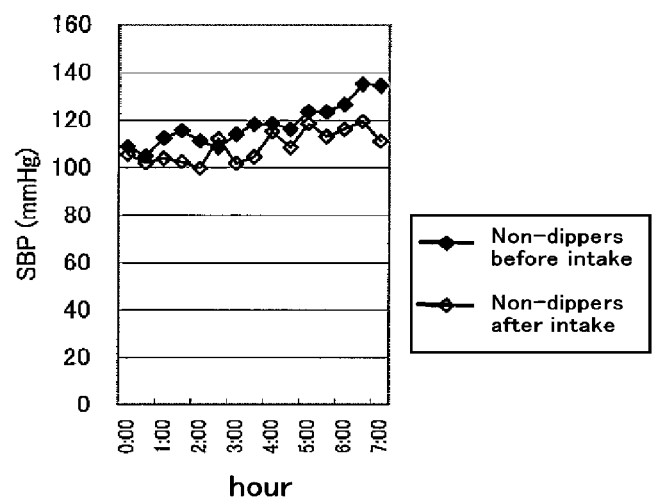
FIG. 2 is a graph comparing SBP profiles in non-dippers before and after the intake of the agent of the present invention for determination of the effect of reducing risk in onset of diseases ascribable to circadian variation in blood pressure, performed in Example 1.

FIGS. 1 and 2 show that, in SBP during the period 0:00-7:00, no significant difference was observed in dippers before and after the intake of the fermented milk product for subjects, whereas significant difference (P<0.05, paired t-test) was observed in non-dippers. It was demonstrated that the fermented milk product for subjects containing the hydrolysate of animal milk protein according to the present invention was capable of effectively reducing systolic blood pressure from night to early morning in normal individuals with normal SBP and DBP but with a particular non-dipping circadian profile of blood pressure as defined in the present invention, and was capable of reducing risk in onset, particularly likely in the morning, of diseases caused by circadian variation of blood pressure. Incidentally, no fluctuation was observed in the heart rate of the subjects during the determination.

What is claimed is:

1. A method for increasing magnitude of nocturnal or early morning decline in mean systolic blood pressure of a non-dipper individual, comprising orally administering a animal milk protein hydrolysate containing Ile-Pro-Pro tripeptide and Val-Pro-Pro tripeptide, or a concentrate thereof, to the non-dipper individual, wherein said non-dipper individual has mean systolic blood pressure (SBP) of less than 130 mmHg and mean diastolic blood pressure (DBP) of less than 80 mmHg, and shows a less than 10% decline in mean systolic blood pressure during a time period of 0:00-5:00 compared to mean systolic blood pressure during a time period of 8:00-21:00, all as measured brachially every 30 minutes with a 24-hour ambulatory blood pressure monitor.

2. The method according to claim 1, wherein said hydrolysate or said concentrate thereof contains the Ile-Pro-Pro tripeptide at 2 to 40 µg/ml, and the Val-Pro-Pro tripeptide at 3 to 60 µg/ml.

3. The method according to claim 1, wherein said hydrolysate or said concentrate thereof is administered at 1 mg to 30 g per day in terms of solids.

4. The method according to claim 1, wherein said hydrolysate or said concentrate thereof is administered continuously or intermittently.

5. The method according to claim 1, wherein said hydrolysate or said concentrate thereof is administered continuously or intermittently for not less than 20 consecutive days.

6. The method according to claim 1, wherein said hydrolysate is a fermentation product obtained by fermentation of a starting material containing animal milk protein, employing lactic acid bacteria.

7. The method according to claim 6, wherein said lactic acid bacteria comprise *Lactobacillus helveticus*.

8. The method according to claim 7, wherein said *Lactobacillus helveticus* is FERM BP-6060.

9. The method according to claim 1, wherein said hydrolysate is a digestion product obtained by enzymatic digestion of a starting material containing animal milk protein, wherein the enzymatic digestion employs enzymes originated from koji mold.

10. The method according to claim 9, wherein said enzymes are originated from *Aspergillus oryzae*.

* * * * *

SEQUENCE LISTING

```
<160> NUMBER OF SEQ ID NOS: 2

<210> SEQ ID NO 1
<211> LENGTH: 3
<212> TYPE: PRT
<213> ORGANISM: Bos Taurus

<400> SEQUENCE: 1

Val Pro Pro

<210> SEQ ID NO 2
<211> LENGTH: 3
<212> TYPE: PRT
<213> ORGANISM: Bos Taurus

<400> SEQUENCE: 2

Ile Pro Pro
```